United States Patent
Mayer et al.

(10) Patent No.: US 11,219,815 B2
(45) Date of Patent: *Jan. 11, 2022

(54) PHYSIOLOGICAL RESPONSE MANAGEMENT USING COMPUTER-IMPLEMENTED ACTIVITIES

(71) Applicant: The Catherine Mayer Foundation, Seattle, WA (US)

(72) Inventors: Catherine Mayer, Seattle, WA (US); Robert Reinhardt, Seattle, WA (US); Michael Woo, Seattle, WA (US)

(73) Assignee: THE CATHERINE MAYER FOUNDATION, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/077,862

(22) Filed: Oct. 22, 2020

(65) Prior Publication Data

US 2021/0077888 A1 Mar. 18, 2021

Related U.S. Application Data

(63) Continuation of application No. 15/890,200, filed on Feb. 6, 2018, now Pat. No. 10,835,802.

(60) Provisional application No. 62/455,998, filed on Feb. 7, 2017.

(51) Int. Cl.
| | |
|---|---|
| *G16H 20/30* | (2018.01) |
| *A63B 24/00* | (2006.01) |
| *A63B 71/06* | (2006.01) |
| *G06F 3/01* | (2006.01) |
| *G06K 9/00* | (2006.01) |

(52) U.S. Cl.
CPC ...... *A63B 71/0622* (2013.01); *A63B 24/0062* (2013.01); *G06F 3/015* (2013.01); *G06K 9/00536* (2013.01); *G16H 20/30* (2018.01)

(58) Field of Classification Search
CPC .............. A63B 71/0622; A63B 24/0062; G16H 20/30; G06F 3/015; G06K 9/00536
See application file for complete search history.

(56) References Cited

U.S. PATENT DOCUMENTS

| | | | |
|---|---|---|---|
| 2004/0150627 A1 | 8/2004 | Luman et al. | |
| 2007/0167690 A1* | 7/2007 | Miyazaki | A61B 5/16 600/300 |
| 2011/0183305 A1 | 7/2011 | Orbach | |
| 2014/0200432 A1 | 7/2014 | Banerji et al. | |
| 2015/0199095 A1* | 7/2015 | Lahtivuori | G06F 3/0482 715/763 |
| 2016/0310073 A1 | 10/2016 | Kusik et al. | |
| 2017/0004860 A1 | 1/2017 | Muller | |

(Continued)

*Primary Examiner* — Andrew T Chiusano
(74) *Attorney, Agent, or Firm* — Seed IP Law Group LLP

(57) ABSTRACT

A system, methods, and techniques are provided for performing automated operations to track one or more physiological indicators of a user via hardware capabilities of a computing device associated with the user, and/or of external monitoring devices communicatively coupled to such a user computing device. Feedback regarding such tracked activities may be provided to the user via one or more guided physiological and/or exercises. The system may enable the user to interactively create and/or experience audiovisual artworks that may include still images, music, dynamic sound effects, and animations, such as animations depicting the creation of one or more related artworks.

20 Claims, 9 Drawing Sheets

(56) References Cited

U.S. PATENT DOCUMENTS

2017/0011210 A1     1/2017  Cheong et al.
2017/0154159 A1*    6/2017  Rahman ................. G11B 27/10
2017/0221253 A1     8/2017  Banerjee et al.
2017/0354795 A1    12/2017  Blahnik et al.
2017/0358240 A1    12/2017  Blahnik et al.

* cited by examiner

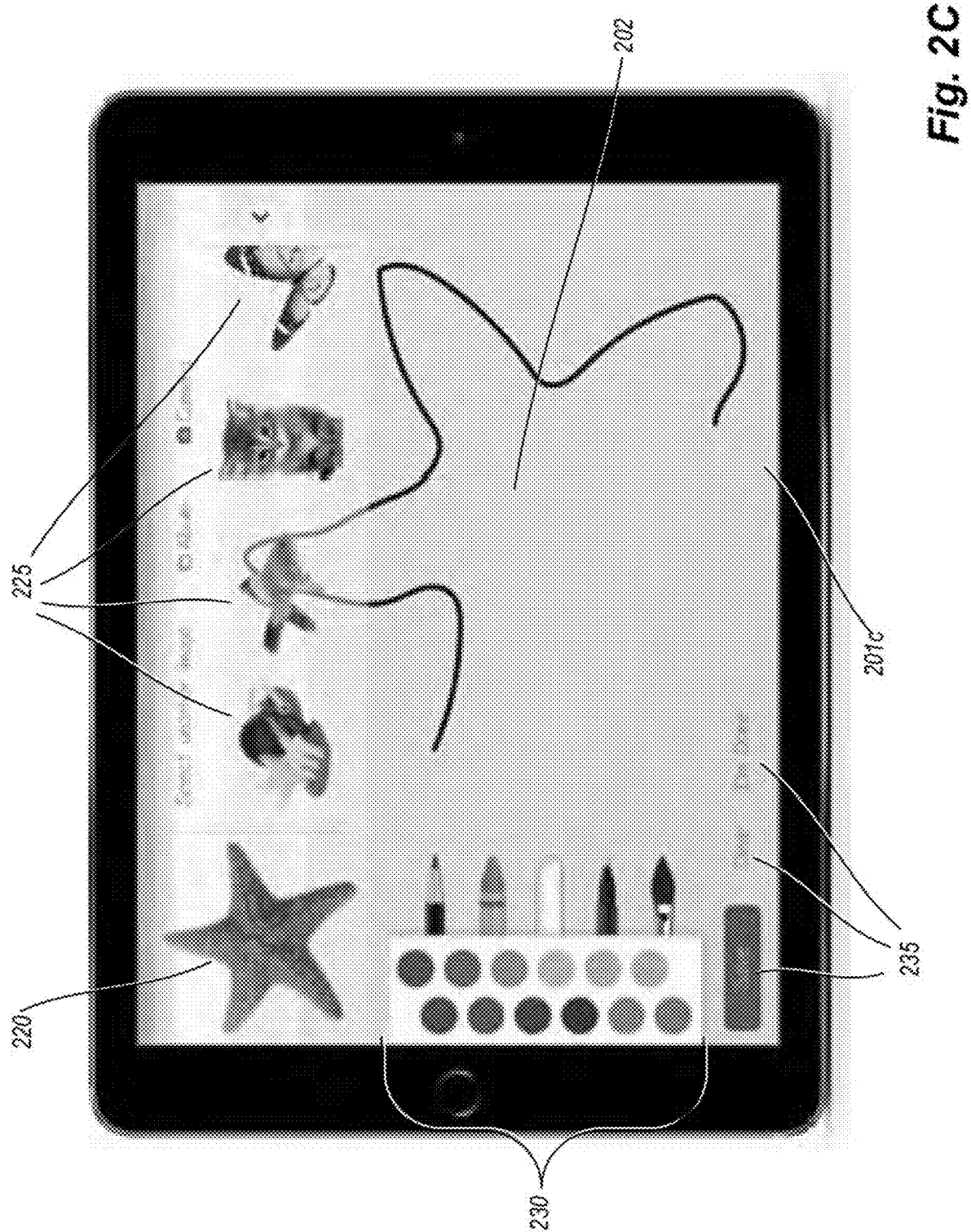

PHYSIOLOGICAL RESPONSE MANAGEMENT USING COMPUTER-IMPLEMENTED ACTIVITIES

CROSS-REFERENCE TO RELATED APPLICATIONS

This application is a Continuation of U.S. patent application Ser. No. 15/890,200, filed Feb. 6, 2018, which application claims the benefit of U.S. Provisional Patent Application No. 62/455,998, filed Feb. 7, 2017 and entitled "Physiological Response Tracking And Management Using Computer-Implemented Activities," both of which are hereby incorporated by reference in their entirety.

TECHNICAL FIELD

The following disclosure relates generally to techniques for tracking, analyzing and using information from physiological responses to presented stimuli and corresponding activities, such as for users interacting with computer-implemented devices to perform computer-directed activities.

BACKGROUND

Various devices exist for tracking human physiological responses to exercise or other activity, such as step counters, heart rate monitors, etc. However, such devices are not typically integrated with or coupled to additional systems that actively direct human activities in order to improve particular physiological responses in particular ways.

In addition, positive responses of human beings to various presented audiovisual stimuli has been documented and explored. For example, shared spaces have benefited from the presentation of interactive multimedia information, which have been shown to increase observer satisfaction levels in comparison to traditional static displays. However, such audiovisual presentations do not typically actively direct human activities in order to improve particular physiological responses in particular ways, or perform any tracking of or feedback involving resulting human physiological responses.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 2A-2D illustrate examples of a graphical user interface provided by an embodiment of the PRMTF system in accordance with the described techniques.

DETAILED DESCRIPTION

Figure 1:
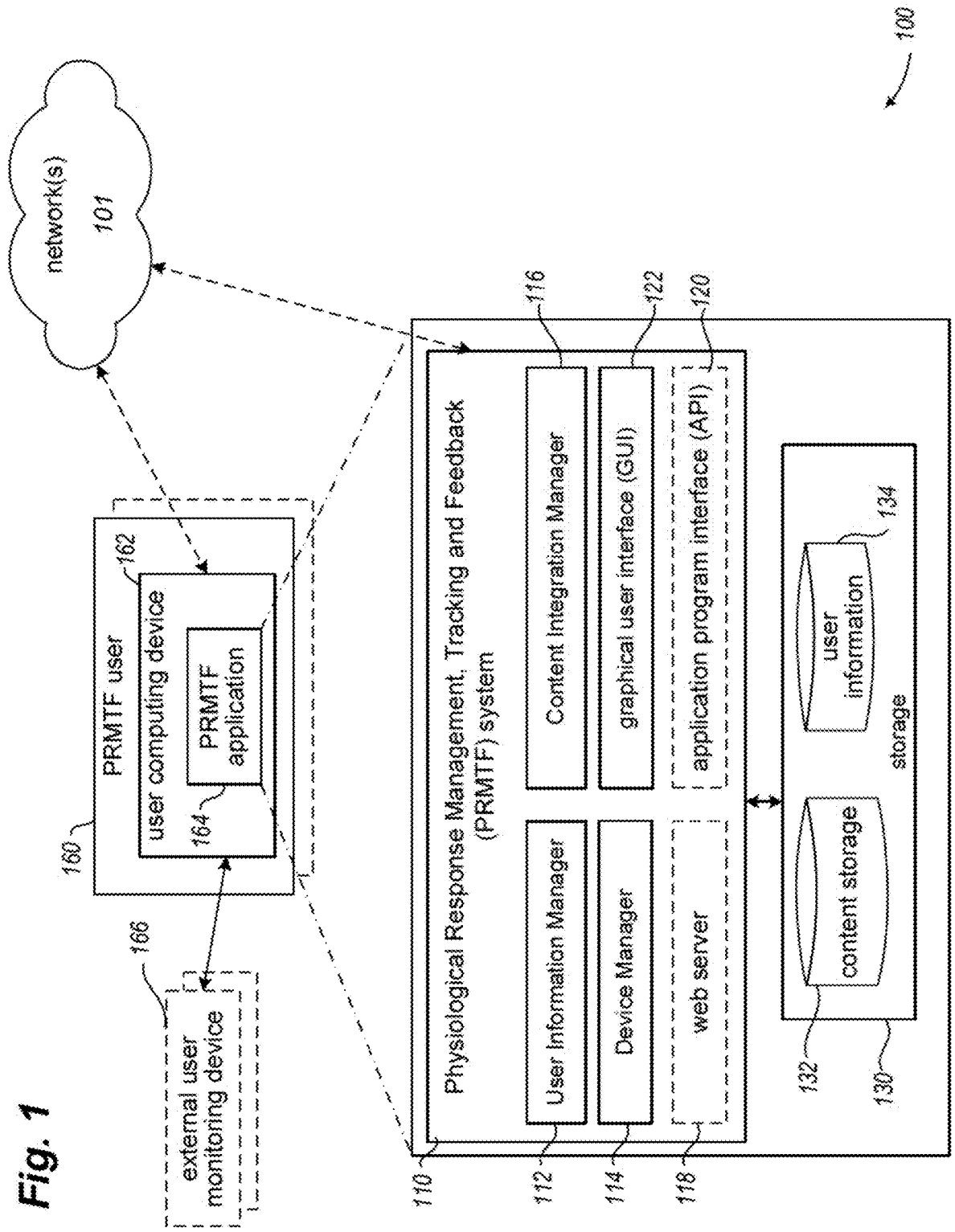
FIG. 1 is a diagram of a networked environment that includes a Physiological Response Management, Tracking and Feedback ("PRMTF") system in accordance with techniques described herein, as well as various computing systems associated with one or more users of the PRMTF system.

Techniques are described by which one or more computing systems perform automated operations for tracking, analyzing and using information from human physiological responses to presented stimuli and corresponding activities, such as for users interacting with computer-implemented devices to perform computer-directed activities. In at least some embodiments, the described techniques include automated operations to direct user movements and other activities of users of client computing devices, and to track, analyze, and use measurements of physiological indicators of the users corresponding to the activities (e.g., stress level, breathing, and heart rate). For example, the described techniques may include providing one or more guided physical exercise activities and/or guided artistic exercises that are designed to regulate one or more human physiological responses of a group that includes breathing, heart rate, blood pressure, stress levels, and endorphins. Using hardware capabilities of a user computing device executing a provided application, and/or hardware capabilities of associated external monitoring devices (e.g., external devices communicatively coupled to such a user computing device), user physiological indicators may be monitored, such as to enable improvement of the physiological indicators concurrently with the activities or over time.

In certain embodiments, some or all of the techniques described herein may be performed by one or more computing systems configured to provide a Physiological Response Management, Tracking and Feedback (PRMTF) system (also referred to at times as a physiological response management system) that provides a corresponding functionality to one or more users of one or more client computing devices. In some embodiments, a copy of the PRMTF system may execute locally on each such client computing device (e.g., as a PRMTF software application, also referred to herein as a "PRMTF application") in order to provide capabilities of the PRMTF system to one or more users of the client computing device, while in other embodiments the PRMTF system may execute remotely from the client computing device(s) to provide an online PRMTF service available to one or more such users over one or more computer networks.

In one or more embodiments, the PRMTF system may track various physiological indicators associated with a user, and may provide feedback regarding such tracked physiological indicators to the user via guided exercises. For example, a software application executing on a device associated with the user may, either separately or in conjunction with the guided exercises, enable the user to interactively create and/or experience audiovisual artwork, with such artwork reflecting one or more aspects of user movement and/or physiological indicators tracked by the PRMTF system, and with such activities designed in some embodiments to improve particular physiological responses. The PRMTF system may initiate the creation of such artwork using a variety of digital media, including one or more of still images, animation, music, dynamic sound effects, and time-lapse recordings of the artwork being created. In other embodiments, the PRMTF system may provide some or all of such described techniques in other manners, such as by directing particular types of movement of a user, whether instead of or in addition to creating artwork using digital media.

In certain embodiments, the tracking of physiological indicators associated with a user by the PRMTF system may include using hardware capabilities of a client device associated with that user. For example, a PRMTF software application executing on a user's client device may use hardware capabilities of the client device in order to detect one or more physiological indicators for the user. As non-limiting examples, tracking the physiological indicators may include receiving signals from the computing device originating via a microphone (e.g., to listen to the user's breathing); a camera, gyroscope, and/or accelerometer (e.g., to track the movement of one or more body parts of the user, including but not limited to the user's fingers, hands, eyes, shoulders, limbs, head, diaphragm, etc.); a pressure-sensitive touchscreen (e.g., to track the user's heart rate via a hand or other body part in contact with the touchscreen); or other suitable hardware capabilities. In at least one embodiment, the PRMTF system may display various animations or other visualizations, as well as play various sounds or music, in order to provide audiovisual feedback to the user regarding one or more physiological indicators tracked in this or other manners by the PRMTF system. As used herein, audiovisual information may include at least one presented audio output and/or at least one presented visual output, with some embodiments and situations having an audiovisual work that includes at least one presented audio output and at least one presented visual output, and with some embodiments and situations having an audiovisual work that includes multiple presented audio outputs and/or multiple presented video outputs.

In addition, in some embodiments the PRMTF application may track physiological indicators of the user based on data from one or more external devices (e.g., external devices communicatively coupled to one or more client computing devices of the user that are executing the PRMTF application), whether instead of or in addition to hardware capabilities of the one or more client computing devices of the user. For example, such external devices may include an exercise monitor (e.g., a "Fitbit" or other exercise monitor), a smart watch or other wearable device, an external microphone, external camera or motion-sensing device (e.g., a Microsoft Kinect or other motion sensor device), one or more other types of bio-feedback devices (e.g., muscular movement of a user triggers a response in information presented to the user by the PRMTF system), etc. As described elsewhere herein, in certain embodiments and scenarios the PRMTF system may provide audiovisual feedback to the user regarding such tracked physiological indicators. In addition, the PRMTF system may in some embodiments perform additional tracking of one or more users, such as to track measurements of time spent by a user in various activities related to the PRMTF system, progress achieved with respect to one or more goals associated with the user, etc. Such goals might include, as non-limiting examples, progress towards optimizing one or more physiological indicators of the user, progress towards one or more application-directed activity goals of the user, etc.

Various example graphical user interface ("GUI") screens for the PRMTF system are presented with respect to particular embodiments shown for illustrative purposes, although it will be appreciated that other embodiments may include more and/or less information, and that various types of illustrated information may be replaced with other information. For example, while these example GUI screens may be appropriate for guiding children through exercises to control or otherwise manage particular physiological responses (e.g., breathing, heart rate, blood pressure, etc.) as part of creating artwork using digital media, other embodiments may involve other types of exercises for other types of users (e.g., adults, humans with a particular type of physical and/or mental disability, humans training to reach a designated level of one or more types of physiological responses, etc.), may control or otherwise manage other types of physiological responses and/or non-physiological responses (e.g., concentration, memory, etc.), may use other types of client devices and/or monitoring equipment, etc.

In particular, FIGS. 2A-2D illustrate examples of providing various functionality with respect to various guided exercises for users of the PRMTF system in one embodiment that involves guiding children through exercises to control or otherwise manage particular physiological responses as part of creating artwork using digital media.

Figure 2A:

FIG. 2A displays a graphical user interface 201a. As depicted, the GUI includes a designated drawing area 202 that includes an image of a target subject 205 (in this case, an apple) along with an animated character 210 (in this case, a bug), both of which are prominently displayed using a large portion of the designated drawing area. During the provided guided exercise, as part of an interaction session with the user, the user may be prompted by the animated character to create a "contour drawing" or other type of impression of the depicted subject by "following" the animated character as it travels along the surface of the apple, such as by visual instructions (not shown) and/or audio instructions. In certain embodiments, the user may "follow" the animated character using a finger, a stylus, or other applicable instrument in conjunction with a touch-sensitive display of the computing device, and may track and provide feedback regarding the location, pace and/or other characteristics of the user's movements. In other embodiments, the PRMTF system may otherwise track one or more other movements of the user as the user moves one or more body parts through a space monitored by the PRMTF system.

Figure 2B:

As another example, FIG. 2B displays a GUI 201b that includes another subject 215 (in this case, a fish), along with a designated drawing area 202. While the animated character 210 of FIG. 2A is not shown in this example, in certain embodiments the PRMTF system may include guided drawing exercises (e.g., as part of a continuing interaction session with the user) in which an animated character travels along a perimeter and/or other portions associated with the subject 215 (the fish). In this example, visual instructions (not shown) and/or audio instructions may be used to direct the user to perform one or more particular activities, such as to reproduce a contour or outline of the subject fish in the drawing area 202, to draw an environment in which the fish lives (e.g., kelp, a shipwreck, other fish, etc.), to draw the visible lines for a portion of the fish (e.g., the upper fin), etc. It will be appreciated that in contrast to the drawing exercise depicted in FIG. 2A, the subject 215 is smaller and positioned adjacent to the designated drawing area 202, as opposed to being centrally located within that designated drawing area. In this manner, for example, the PRMTF system may provide the user with a greater sense of freedom when drawing the subject or other display.

As another example, FIG. 2C displays a GUI 201c that includes another subject 220 and designated drawing area 202. While not depicted as part of FIG. 2C, the PRMTF system may additionally display an animated character or other element in order to guide the user in certain embodiments, as with the drawing exercises depicted in FIGS. 2A and 2B (e.g., as part of a continuing interaction session with the user). In contrast to the earlier drawing exercises depicted in FIGS. 2A and 2B, the PRMTF system displays a number of additional possible subjects 225 from which the user may select, and may provide visual instructions (not shown) and/or audio instructions to direct the activities of the user. In various embodiments, the PRMTF system may make additional two-dimensional or three-dimensional subjects available to the user. For example, in at least one embodiment, the user may add three-dimensional modeled objects into the drawing workspace of the PRMTF application, optionally from one or more images imported by the user into the application, to allow the user to manipulate, enlarge, shrink, or rotate the modeled object to create new subjects for use in one or more guided exercises or modes of the PRMTF application—as one example, a user may import an image of a shape that they make with their own body, in order to subsequently create a contour drawing of it. In addition, camera filters may be provided to make real objects into colored shapes and/or outlines that the PRMTF system may then analyze and use for drawing exercises (e.g., to create a trail around objects in a scene for the user to follow with his/her finger or stylus).

The GUI 201c of FIG. 2C further includes drawing tools 230 (a variety of instruments and a color palette) and additional drawing controls 235 (allowing the user, in this example, to save the drawing, clear the designated drawing area, or end the current drawing exercise. In addition to button-based user interface elements, controls used within this and other graphical user interfaces provided by the PRMTF system may include system-provided and/or user-defined gesture-based control schemes, such as to play, pause, or alter the rate at which audiovisual content is displayed (or to initiate other functionality), such as for a continuing interaction session with the user, by using various combinations of gestures. Such gestures may be made, for example, while the user is in contact with a touch-sensitive display, or in a space monitored by one or more movement tracking devices. In certain embodiments, the PRMTF system may utilize hardware capabilities of a user computing device such as a gyroscope and accelerometer to provide or augment one or more tools, such as by allowing movement of the user computing device to augment positions or texture of elements of an audiovisual artwork. In this manner, for example, the user might tilt the computing device in order to simulate the pouring or spilling of paint onto a digital canvas displayed by the PRMTF system, or the PRMTF system may use user touch selections on portions of the display to simulate resulting sounds (e.g., from drums, a keyboard, etc.). In addition, over types of drawing backgrounds or artwork creation environments may be provided in at least some embodiments, such as a "zen garden" type of sand movement, finger painting, paint splashing, sculptural activities, color mixing, etc.

The PRMTF system may also provide additional tools as part of the audiovisual artwork creation process in some embodiments, either via one or more guided exercises or as part of one or more provided modes. As non-limiting examples, the PRMTF system may provide, in various scenarios and embodiments, one or more of the following: tools to facilitate the creation or inclusion of audio works, such as to incorporate ambient music and/or ambient sound effects within one or more artworks (e.g., background rain sounds, such as from a rain drum), to record original music or sound effects by the user (e.g., by providing interface elements similar to one or more musical instruments with which the user may interact to produce audio output), etc.; tools to play selected music and/or sound effects as an aid to the user during the artwork creation process; tools to record photographs or other images taken by the user while operating the PRMTF system to produce visual output; tools to import digital content to the PRMTF system from one or more external sources; tools to record the creation of an audiovisual artwork by one or more users, such as for later playback or use as an element in one or more other audiovisual artworks, and/or to share with other users; tools to facilitate collaboration (such as real-time collaboration) between two or more users of the PRMTF system with respect to the creation of one or more audiovisual artworks; etc. As non-exclusive examples of such use of user-generated audiovisual output, an audiovisual work created by a user may be selected (e.g., automatically by the PRMTF system, such as randomly or based on one or more defined criteria; as designated by the user, such as via a control selected in a displayed GUI, etc.), and may be displayed or otherwise presented to one or more other users (and optionally to the creating user), such as in a classroom, a clinic, a lobby or other internal or external public space, etc. As part of the presentation of the audiovisual work, it may optionally be combined with additional audio and/or visual information, such as to combine audiovisual works that are independently created by multiple users (e.g., at different times, simultaneously, etc.), to select and use prerecorded or otherwise predefined groups of audio and/or visual information together with the selected audiovisual work(s) of the user(s), to combine multiple audiovisual works separately created by a user, etc.

Figure 2D:
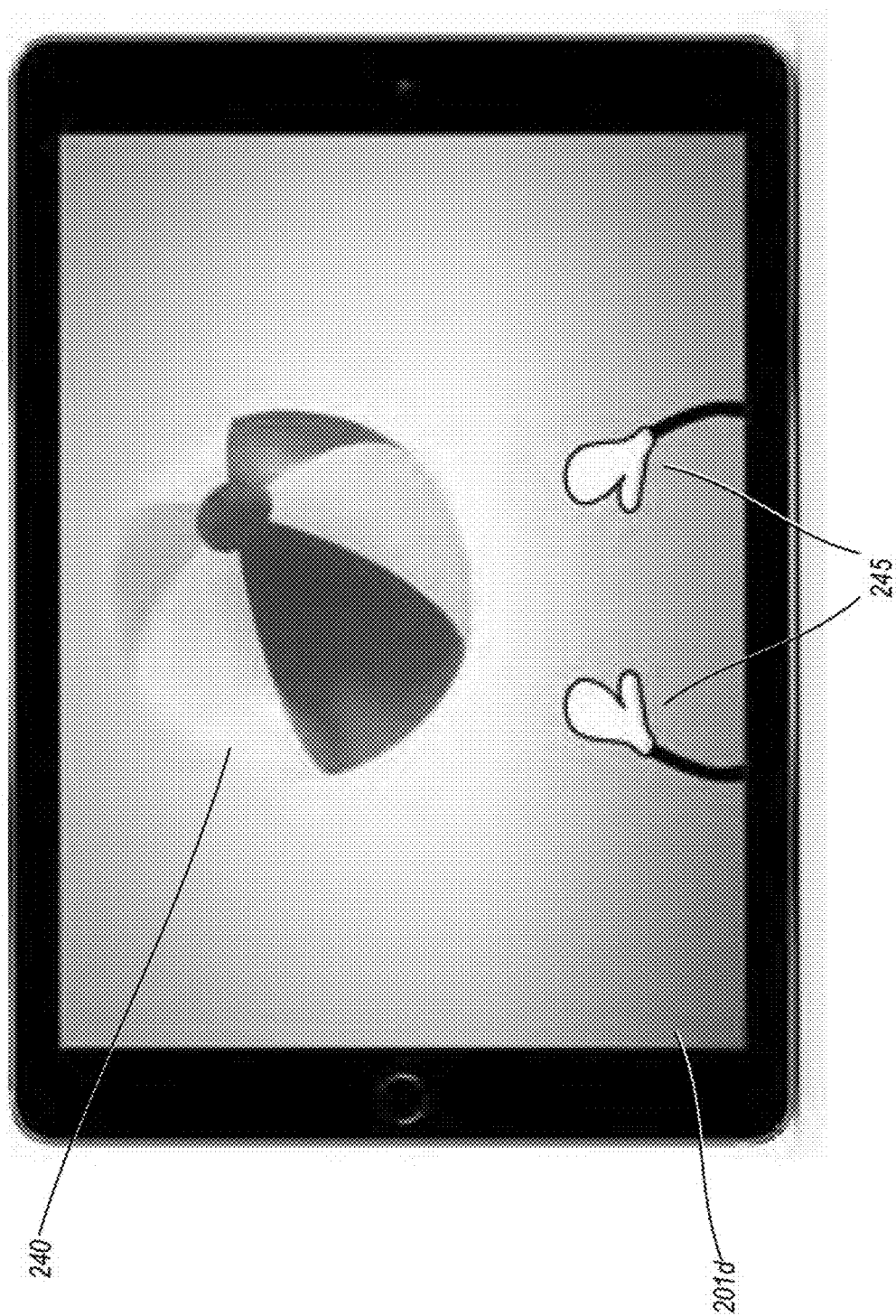

FIG. 2D illustrates a GUI 201d depicting a static image from a guided physiological exercise in which the user's breathing (tracked via hardware components of the user computing device or via one or more external devices communicatively connected to the user computing device, as discussed in greater detail elsewhere herein) is used to move a beach ball 240 up and down on the display screen of the user computing device (e.g., as part of a continuing interaction session with the user). In the illustrated embodiment, portions 245 of an animated character is also depicted, such as to provide context for movement of the animated beach ball. In various embodiments, the PRMTF system may first display the animation in a manner such that the subject beach ball moves according to an optimal breathing rate determined for the user (or otherwise according to a determined target breathing rate, whether specific to the user or as a default, and whether specified by the user and/or by the PRMTF system), such as to illustrate for the user a breathing rate that may most efficiently effectuate physiological calming. Following the initial display of that animation in the optimized manner, display of the animation may be modified by the PRMTF system to adopt a rate matching the tracked physiological indicators—i.e., to allow the user's own breathing to influence the rate at which the animated beach ball rises and falls. The PRMTF system may monitor and track the current breathing rate of the user, and provide feedback both by altering the rate at which the animation is displayed and possibly providing audio feedback (e.g., music, dialogue, or sound effects), in order to encourage the user to increase or decrease their rate of breath accordingly. Other types of breathing-related activities may also be used in other embodiments and situations, such as various types of rhythmic breathing (e.g., following different animals, monitoring of breathing at different times, manipulation of animations on screen in accordance to breathing). In addition, it will be appreciated that user activities and/or physiological indicators other than breathing may similarly be used in some embodiments, whether instead of or in addition to breathing.

Guided physiological exercises such as that described above with respect to FIG. 2D may also be provided independently of, or in conjunction with, other user activities within the PRMTF system, such as part of the same user interaction session or a different user interaction session. For example, in certain scenarios and embodiments the PRMTF system may initiate guided physiological exercises prior to (and/or in preparation for) initiating an artistic mode (e.g., drawing or other exercises, or an "open draw" mode in which the user may freely draw without guidance from the PRMTF system or application).

It will be appreciated that the details of the examples of FIGS. 2A-2D are provided for non-limiting illustrative purposes, and that some embodiments may lack some or all of the details of these examples.

As used herein, the term "user" may refer to any human or other entity interacting with the PRMTF system or PRMTF application. The term "selecting," when used herein in relation to one or more elements of a graphical user interface or other electronic display, may include various user actions taken with respect to various input control devices depending on the client computing device used to interact with the display, such as one or more clicks using a mouse or other pointing device, one or more tapping interactions using a touch screen of a client device, etc. In addition, in certain embodiments "selecting" or other interactions with the PRMTF system may be effectuated by a user moving one or more body parts through a physical space monitored for movement by the PRMTF system, such as using one or more predefined gestures in conjunction with a movement monitoring device.

In one or more embodiments, the PRMTF system may provide guided exercises for the user related to one or more endeavors using a PRMTF application, such as may be executing on a client device associated with the user. For example, in certain embodiments the PRMTF application may display visual and/or auditory prompts to the user as the user traces, or otherwise represents, an object or objects that the PRMTF application displays on the user's client computing device.

In at least some embodiments, the PRMTF system may provide one or more guided physiological exercises, such as to educate and/or facilitate the user in mindfully controlling the user's body to effectuate physiological calming or other desired effects. Moreover, the PRMTF system may in certain embodiments track and provide feedback or other results as part of such physiological exercises, such that (as one example) animations are displayed to the user in a manner that is altered in accordance with an optimal or desired value for one or more of the physiological indicators tracked by the PRMTF system. In at least one embodiment, such guided physiological exercises may be provided by the PRMTF system in conjunction with, or preceding, guided exercises as described elsewhere herein, such as to provide benefits of physiological calming with respect to creating one or more audiovisual artworks. Furthermore, in certain embodiments and scenarios, guided exercise may be provided by the PRMTF system with respect to additional user activities, such as to facilitate individual or collaborative gestures, dance and/or yoga and/or other movements using the PRMTF application, and may include recordings or other reproductions of such movements in audiovisual artwork or other productions via the PRMTF system.

In at least some embodiments, the PRMTF system may provide distinct and separate interfaces, control options, guided exercises, and audiovisual content based on one or more characteristics of the user. For example, the PRMTF system may provide more simplistic and colorful guided exercises for child users of the PRMTF system in comparison to those provided to adult users, and may additionally include distinct options for particular animated characters to use in conjunction with such guided exercises. In addition, the PRMTF system may provide various customization options related to such guided exercises and other content, such as based on user preferences with respect to color, format, complexity, or other preferences. Moreover, in certain embodiments the PRMTF system may provide distinct and separate options for users with one or more disabilities, such as visually impaired users or auditory impaired users. Thus, the GUI presented to the user may enable or cause the user to more efficiently make selections of presented information or otherwise use presented information.

In addition, in various scenarios and embodiments, audiovisual artwork created by users and/or affiliates of the PRMTF system may be provided to one or more client installations, such as in order to display interactive and/or dynamic multimedia artwork in public or private spaces associated with clients of the PRMTF system. For example, such artwork may be provided by the PRMTF system for display in healthcare offices, clinics, schools (e.g., classrooms), commercial buildings (e.g., lobbies, offices, etc.), art installations, or other shared spaces that might traditionally host static artwork. In some embodiments, the storage and/or playback of audiovisual artwork created by users and/or affiliates of the PRMTF system may be enhanced by capturing the creation of the artwork in a way that allows the playback to occur in an animated manner (e.g., by recreating each stroke made to create a drawing in the same order as the original, whether at the same speed as during the original creation or at an altered speed, such as 5 times or 10 times as fast, at a designated fraction as fast, etc.; by individually playing back multiple simultaneous or otherwise overlapping sounds rather than recording and playing back a single blended resulting sound, whether at the same speed as during the original creation or at an altered speed; etc.). For example, when creating visual information that is based at least in part on strokes from a user's finger, stylus or other drawing implement, each stroke may be captured as a series of points (e.g., with corresponding location, as well as other metadata such as time, color, line thickness, etc.), and optionally represented as the captured point data or instead as a straight line or other curve in the stored information—subsequently, the same series of points (or a close approximation of them) may be recreated at time of presentation (whether directly from stored point data or from a stored line/curve approximation that represents them, along with using some or all metadata information from the original capture), as an animated recreation of the original drawing and/or as the resulting final product. In addition, as part of a playback, one or more such user-created visual artworks may be selected (e.g., for use in a sequential playlist or having one or more other designated orders), whether by a user on whose device(s) the presentation will occur and/or by other users (e.g., a creator on one or more of the artworks, an administrative user of the PRMTF system, etc.), and the system may provide the selected artwork(s) to the destination device(s) for presentation (e.g., from a central server of the PRMTF system, for one or more individual client devices of users, etc.), such as in a streaming manner or via a download that occurs before the presentation begins. Such a playback of one or more such user-created audiovisual artworks may further in some embodiments be accompanied by simultaneous presentation of other audiovisual information (e.g., for visual user-created artwork, to accompany its display or other presentation with audio information, whether user-created or created separately and provided or identified by the system, such as one or more commercially created songs; for audio user-created artwork, to accompany its presentation with visual information, whether user-created or created separately and provided or identified by the system; etc.)—as with the user-created audiovisual artwork itself, such other simultaneously presented audiovisual information may be selected or otherwise specified in various manners in various embodiments (e.g., by the user(s) on whose device(s) the presentation will occur, by users who participate in the creation of the user-created audiovisual artwork, by an administrator user of the PRMTF system, etc.). It will also be appreciated that some user-created audiovisual works may include both audio and video, and that a playlist or other selection of multiple user-created audiovisual works may in some cases include audiovisual works from multiple users that are presented sequentially and/or simultaneously at time of presentation. As one non-exclusive example, multiple students in a classroom or school may each create one or more audiovisual works, and some or all of those various student-created audiovisual works may be subsequently presented on display devices in the classroom or at the school (e.g., in a lobby)—in such a system, one or more teachers or other school personnel may control at least some of the presentation, such as to approve or otherwise select particular audiovisual works before they are included in the subsequent presentation, to control time and location of presentation, to include other simultaneous audiovisual information to present, etc.

FIG. 1 is a schematic diagram of a networked environment 100 that includes a Physiological Response Management, Tracking and Feedback ("PRMTF") system 110, one or more users 160 of the PRMTF system, and one or more user client computing devices 162 associated with those users.

Figure 3:
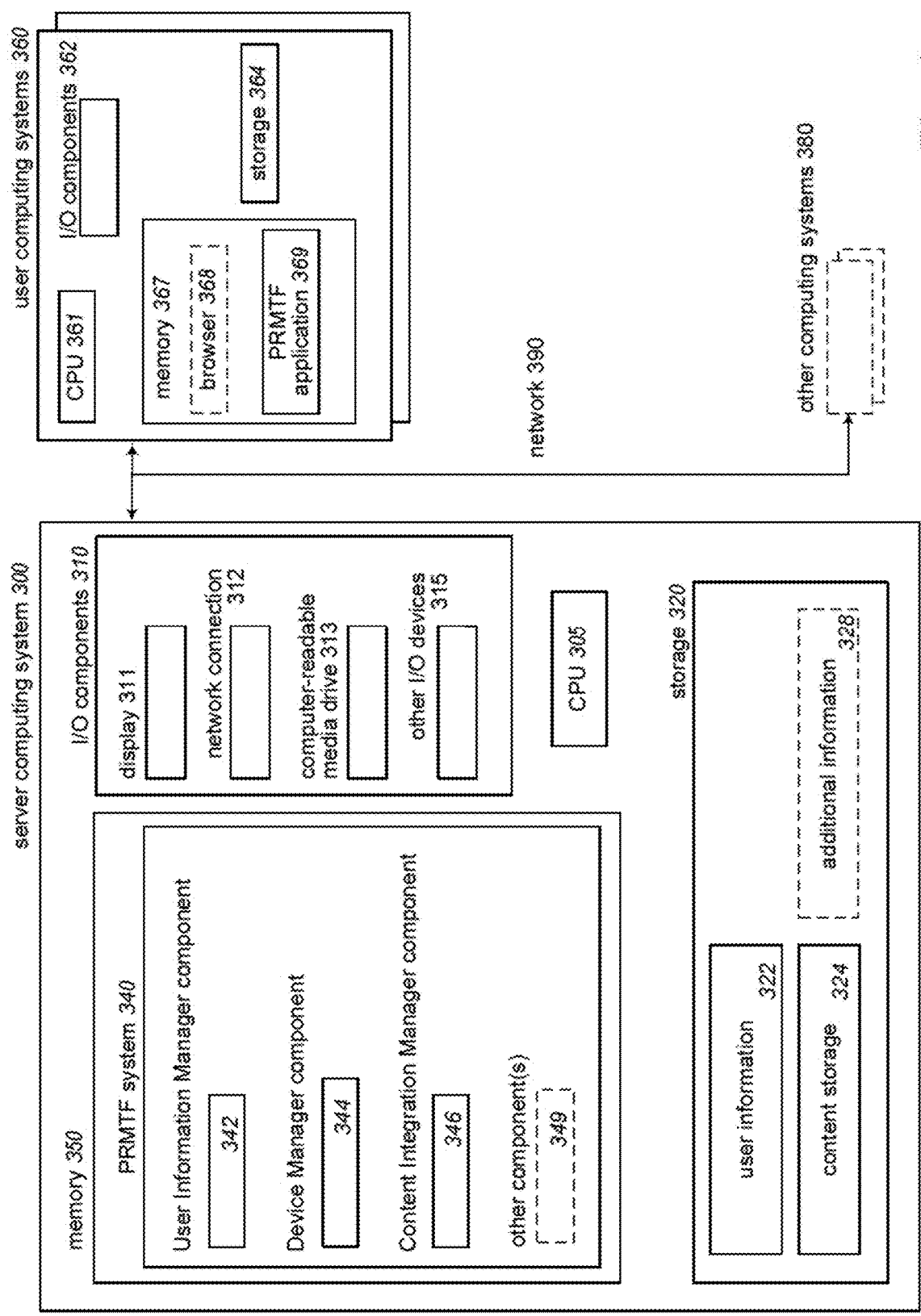
FIG. 3 is a block diagram illustrating example configured computing systems that are suitable for performing at least some of the described techniques.
Figure 4A:
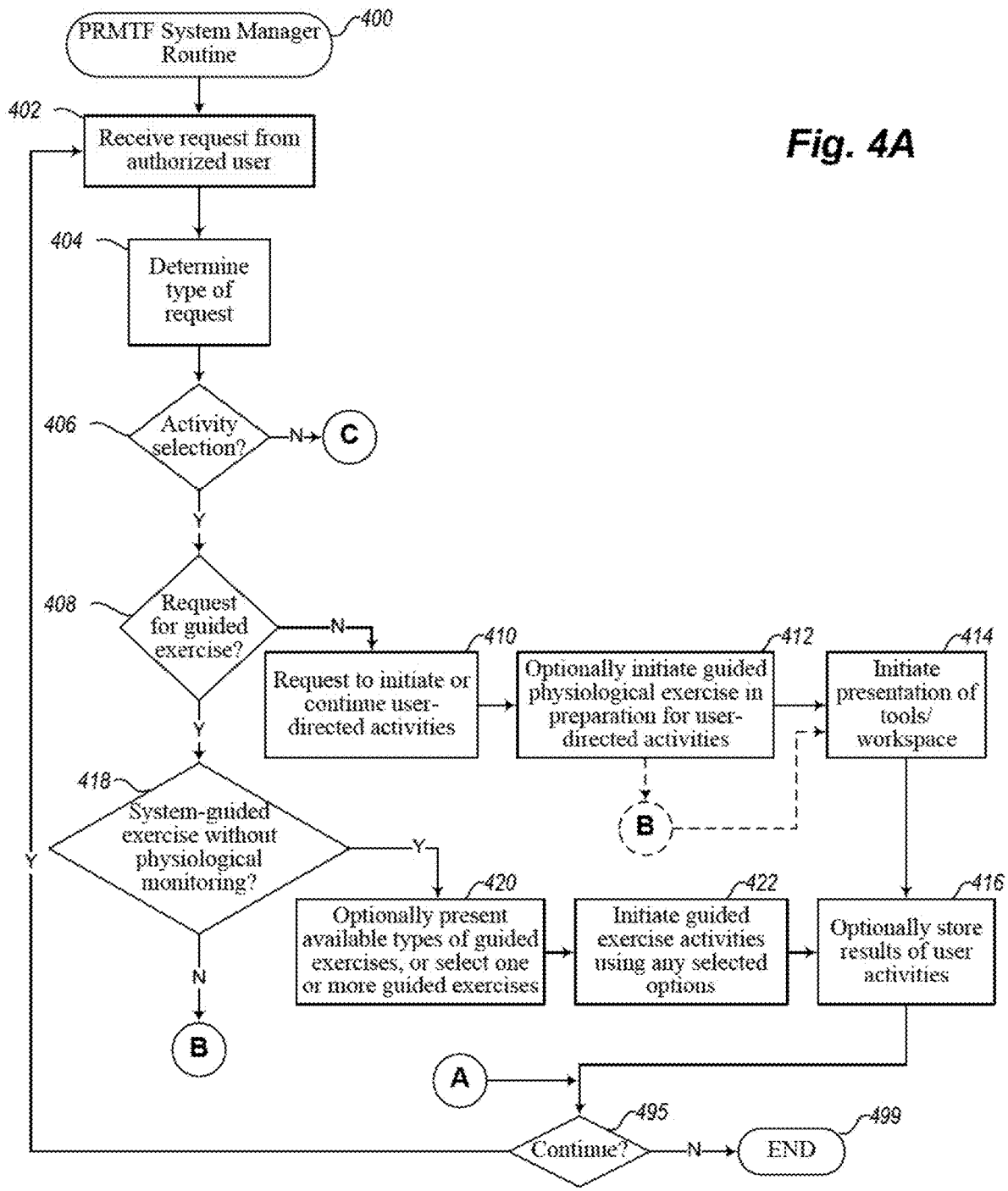
FIGS. 4A-4C are flow diagrams illustrating various operations of an embodiment of the PRMTF system in accordance with the described techniques.
Figure 4B:
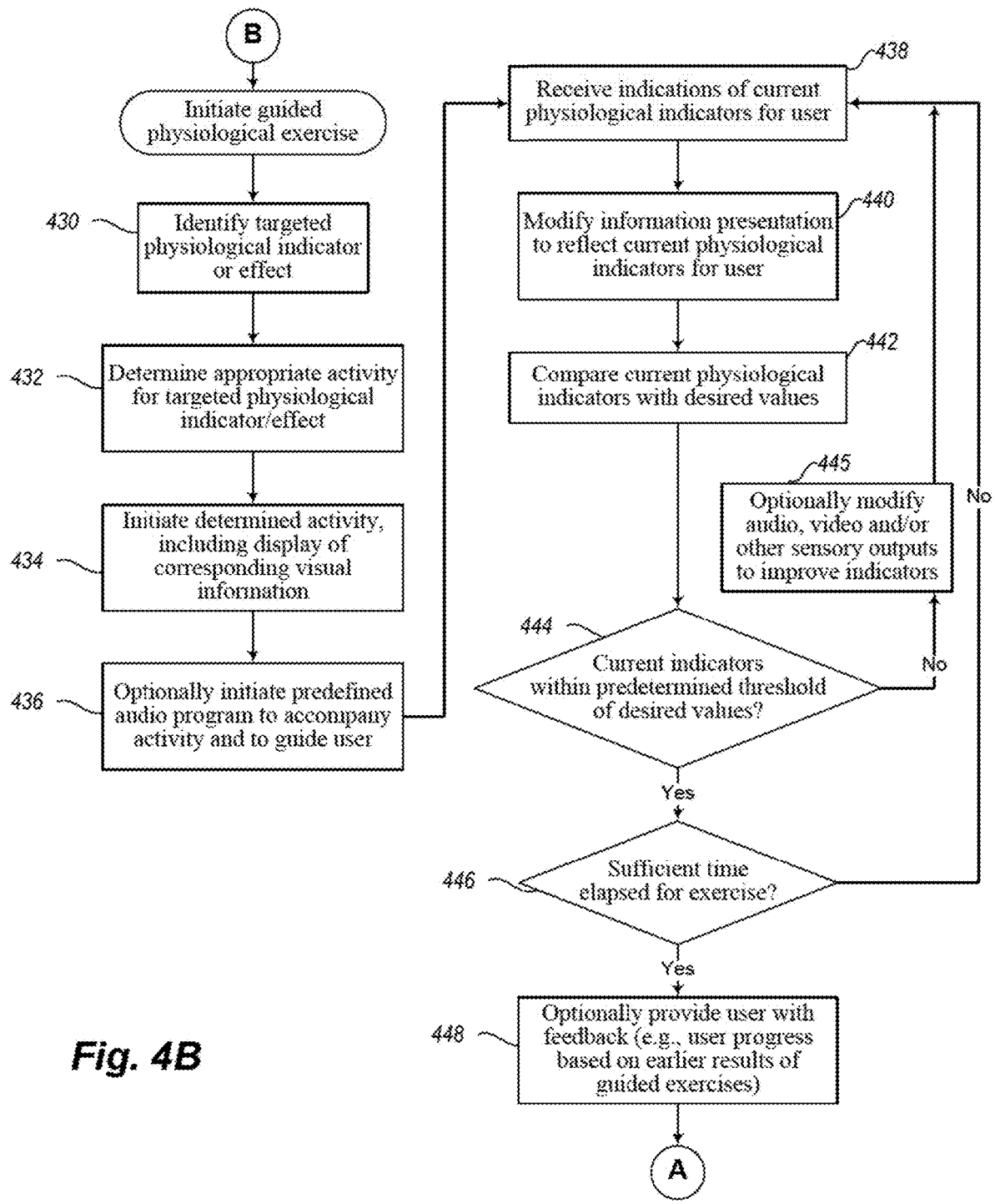
Figure 4C:
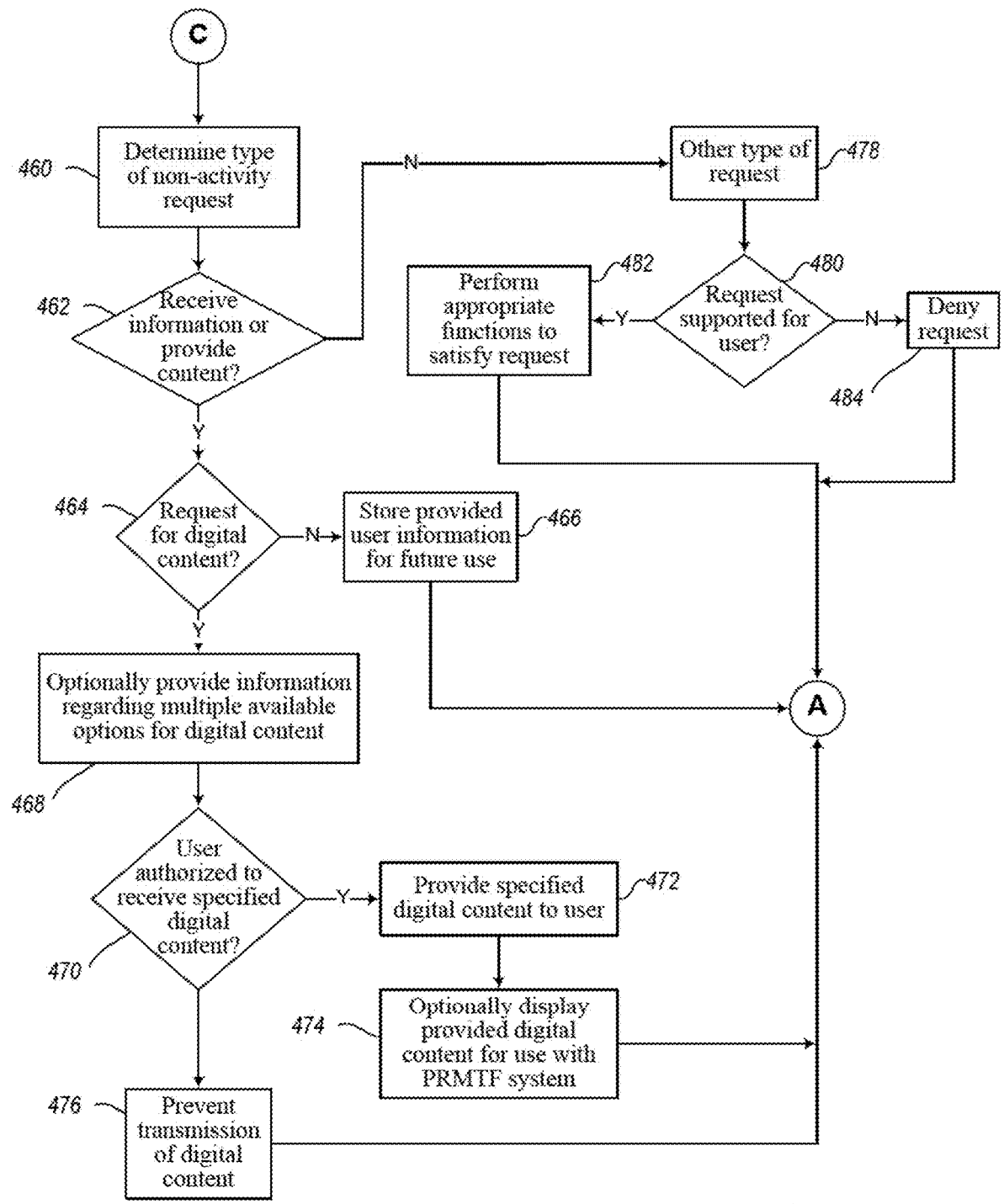

In the depicted embodiment, the PRMTF system 110 includes a user information manager component 112, a device manager component 114, a content integration manager component 116, and a graphical user interface (GUI) 120, with the components 112-116 being discussed in greater detail with respect to FIGS. 3-4C. In some embodiments, copies of the PRMTF system 110 may execute locally on each of one or more user client computing devices 162, such as part of a PRMTF software application 164 that executes locally on a client device to provide functionality of the PRMTF system to one or more users of that client device. In other embodiments, the PRMTF system may execute remotely from one or more of the user client computing devices 162, such as on one or more remote computing systems (not shown)—if so, such embodiments of the remote PRMTF system may also include a web server 118 and/or an application programming interface ("API") 120 for use in communicating over one or more intervening networks 101 with client devices of users. In yet other embodiments, such functionality of the PRMTF system may be provided remotely from some or all user client computing devices 162, and those client devices may each execute a copy of the PRMTF software application 164 to perform interactions over the networks 101 to access functionality from the remote PRMTF system, although in other embodiments such client devices may access functionality from a remote PRMTF system in other manners (e.g., using a web browser, not shown, that is executing locally on a client device to interact with the web server 118 of the remote PRMTF system).

The illustrated example of FIG. 1 includes the one or more user computing devices 160, which may optionally be communicatively coupled to one or more external user monitoring devices 166. Such external user monitoring devices may, if present, include motion trackers, fitness trackers, smart watches or other wearable devices, etc. In addition, each user client computing device 162 may include various hardware (not shown) that may be used by the PRMTF application on that client device, such as microphones, cameras, pressure-sensitive touchscreens, gyroscopes, accelerometers, heart rate sensors, fingerprint sensors, etc.

The PRMTF system is communicatively coupled (locally or remotely) to storage facility 130, which includes content storage database 132 and user information database 134. In certain embodiments, the storage facility 130 may be incorporated within or otherwise directly operated by the PRMTF system; in other embodiments, some or all of the functionality provided by the storage facility may be provided by one or more third-party network-accessible storage service providers. If a local PRMTF application on a client device is implementing the PRMTF system, the storage 130 may be provided in whole or in part on that client device and/or on one or more remote storage devices that are accessed over the network 101.

The interactions of users 160 (and other entities) with the PRMTF system 110 may occur in various ways, such as in an interactive manner via a graphical user interface 122 that is provided by the PRMTF system to those users (e.g., via screens displayed locally on a client device by a PRMTF application executing on that client device; via Web pages or other information screens transferred over the networks 101 by a remote PRMTF system, such as from a Web site provided by Web server 118; etc.). Information from a remote PRMTF system may also be provided in a programmatic manner via the application programming interface ("API") 120, such as to allows computing systems and/or programs to invoke such functionality programmatically (e.g., using Web services or other network communication protocols). As used herein, a client computing device associated with a user may be fixed or mobile, and may include instances of various computing devices such as, without limitation, desktop or other computers (e.g., tablets, laptops, slates, etc.), smart phones and other cell phones, database servers, network storage devices and other network devices, consumer electronics, digital music player devices, handheld gaming devices, PDAs, pagers, electronic organizers, Internet appliances, gaming systems, television-based systems (e.g., using set-top boxes and/or personal/digital video recorders), and various other consumer products that include appropriate capabilities.

In addition to directing activities of users and tracking and using various physiological indicators associated with the user, the PRMTF system may also perform other activities in at least some embodiments (e.g., by a remote PRMTF system exchanging electronic communications with client computing devices associated with the users 160). For example, a user may interact with the PRMTF system in order to register as a new user with the PRMTF system; to provide fees to the PRMTF system (in embodiments in which it charges such fees, such as subscription usage fees or charges associated with acquiring content from the PRMTF system); to provide various information regarding the user (e.g., contact information; financial information, such as to facilitate payments provided to or received from the PRMTF system; user preference information; location information; etc.); etc.

The PRMTF system may further perform automated operations to track, collect, integrate and use some or all of the information received and stored related to a particular user—for example, a PRMTF Web site may present one or more views of the user's integrated information or stored works to the user using a graphical user interface ("GUI") or in other manners.

The PRMTF system may, in various embodiments, enable users of user computing devices 162 (or other computing systems) to obtain related information, such as to view information about, search for, browse for, and/or provide digital content available for transmission and display by the PRMTF system 110, and in certain embodiments to view other additional information (e.g., user account information, preference information, etc.) stored by the PRMTF system. Such digital content may include, for example, one or more of a group that includes completed audiovisual artworks, content related to one or more guided exercises available via the PRMTF system, additional subjects for use in guided exercises of the PRMTF system (including, in certain embodiments, two-dimensional or three-dimensional subjects), etc. Once transmitted to the requesting user, the digital content may be used in various manner, such as displayed and/or stored locally. Such providing of completed audiovisual artworks or other information from the PRMTF system may further allow users of the PRMTF system to share information in some embodiments, such as to send designated information to other designated users or sites (e.g., a social networking site, a shared bulletin board for users of the PRMTF system, etc.).

In the depicted example of FIG. 1, the network 101 may be a publicly accessible network of linked networks, possibly operated by various distinct parties, such as the Internet, although in other embodiments the network 101 may have other forms. For example, the network 101 may instead be a private network, such as, a corporate or university network that is wholly or partially inaccessible to non-privileged users. In still other embodiments, the network 101 may include both private and public networks, with one or more of the private networks having access to and/or from one or more of the public networks. Moreover, in certain embodiments, the various users and providers of the networked environment 100 may interact with the PRMTF system and/or one or more other users and providers using an optional private or dedicated connection, such as dedicated connection 102 as depicted between client installation computing system 180 and the PRMTF system 110. As one example, dedicated connections 102 may include one or more VPN (Virtual Private Network) connections.

FIG. 3 is a block diagram illustrating example computing systems that are configured to perform at least some of the techniques described herein. As noted above, In some embodiments, copies of the PRMTF system may execute locally on each of one or more user client computing devices, such as within a PRMTF software application that executes locally on a client device to provide functionality of the PRMTF system to one or more users of that client device. In other embodiments, the PRMTF system may execute remotely from one or more of the user client computing devices, such as on one or more remote computing systems. In the illustrated embodiment, such a remote PRMTF system 340 is illustrated as executing on one or more server computing systems 300, although in other embodiments such a remote PRMTF system may not be used, and instead the copies of the PRMTF application 369 on the user computing systems 360 may instead provide the functionality of the PRMTF system.

In the particular embodiment depicted, the server computing system 300 includes one or more hardware central processing units ("CPU") or other processors 305, various hardware input/output ("I/O") components 310, storage 320, and memory 350, with the illustrated I/O components including a display 311, a network connection 312, a computer-readable media drive 313, and other I/O devices 315 (e.g., keyboards, mice or other pointing devices, microphones, speakers, GPS receivers, etc.). The server computing system 300 and PRMTF system 340 may communicate with other computing systems via one or more networks 390 (e.g., the Internet, one or more cellular telephone networks, etc.), such as with user computing systems 360 and/or other computing systems 380. The illustrated user computing systems 360 and other computing systems 380 may each have components similar to those of server computing system 300, including (with respect to user computing systems 360) one or more hardware CPUs 361, I/O components 362, memory 367 and storage 364, although some details of such components are not illustrated here for the sake of brevity.

In the illustrated embodiment, an embodiment of the PRMTF system 340 executes in memory 350 in order to perform at least some of the described techniques, such as by using the processor(s) 305 to execute software instructions of the system 340 in a manner that configures the processor(s) 305 and computing system 300 to perform automated operations that implement those described techniques. In other embodiments in which the PRMTF system executes locally on a particular computing system 350 as part of a PRMTF application 369 on that computing system 350, the application 369 may similarity execute in memory 367 of the computing system 350 to perform at least some of the described techniques, such as by using the processor(s) 361 of that computing system 350 to execute software instructions of that application 369 in a manner that configures the processor(s) 361 and computing system 350 to perform automated operations that implement those described techniques. As part of such automated operations (whether on the server computing system 300 and/or on a particular user computing system 350), the PRMTF system 340, user information manager component 342, device manager component 344, content integration manager component 346, and/or other optional executing programs or components 349 may store, retrieve and use various types of data, including in the example database data structures of storage 320. In this example, the data used may include various types of user information in database ("DB") 322, various types of content storage in DB 324, and various types of optional additional information in DB 328.

It will be appreciated that computing system 300, 360 and 380 are merely illustrative and are not intended to limit the scope of the present invention. The systems and/or devices may instead each include multiple interacting computing systems or devices, and may be connected to other devices that are not specifically illustrated, including through one or more networks such as the Internet, via the Web, or via private networks (e.g., mobile communication networks, etc.). More generally, a device or other computing system may comprise any combination of hardware that may interact and perform the described types of functionality, optionally when programmed or otherwise configured with particular software instructions and/or data structures, including without limitation desktop or other computers (e.g., tablets, laptops, slates, etc.), database servers, network storage devices and other network devices, smart phones and other cell phones, consumer electronics, wearable and other fitness tracking devices, biometric monitoring devices, digital music player devices, handheld gaming devices, PDAs, wireless phones, pagers, electronic organizers, Internet appliances, television-based systems (e.g., using set-top boxes and/or personal/digital video recorders), and various other consumer products that include appropriate communication and/or physiological monitoring capabilities. In addition, the functionality provided by the illustrated PRMTF system 340 may, in some embodiments, be distributed in various components. Similarly, in some embodiments, some of the functionality of the PRMTF system 340 may not be provided and/or other additional functionality may be available.

It will also be appreciated that, while various items are illustrated as being stored in memory or on storage while being used, these items or portions of them may be transferred between memory and other storage devices for purposes of memory management and data integrity. Alternatively, in other embodiments some or all of the software components and/or systems may execute in memory on another device and communicate with the illustrated computing systems via inter-computer communication. Thus, in some embodiments, some or all of the described techniques may be performed by hardware means that include one or more processors and/or memory and/or storage when configured by one or more software programs (e.g., the PRMTF system 340 and/or PRMTF client application 369) and/or data structures, such as by execution of software instructions of the one or more software programs and/or by storage of such software instructions and/or data structures. Furthermore, in some embodiments, some or all of the systems and/or components may be implemented or provided in other manners, such as by consisting of one or more means that are implemented at least partially in firmware and/or hardware (e.g., or instead as one or more means implemented in whole or in part by software instructions that configure a particular CPU or other processor), including, but not limited to, one or more application-specific integrated circuits (ASICs), standard integrated circuits, controllers (e.g., by executing appropriate instructions, and including microcontrollers and/or embedded controllers), field-programmable gate arrays (FPGAs), complex programmable logic devices (CPLDs), etc. Some or all of the components, systems and data structures may also be stored (e.g., as software instructions or structured data) on a non-transitory computer-readable storage mediums, such as a hard disk or flash drive or other non-volatile storage device, volatile or non-volatile memory (e.g., RAM or flash RAM), a network storage device, or a portable media article (e.g., a DVD disk, a CD disk, an optical disk, a flash memory device, etc.) to be read by an appropriate drive or via an appropriate connection. The systems, components and data structures may also in some embodiments be transmitted via generated data signals (e.g., as part of a carrier wave or other analog or digital propagated signal) on a variety of computer-readable transmission mediums, including wireless-based and wired/cable-based mediums, and may take a variety of forms (e.g., as part of a single or multiplexed analog signal, or as multiple discrete digital packets or frames). Such computer program products may also take other forms in other embodiments. Accordingly, embodiments of the present disclosure may be practiced with other computer system configurations.

FIGS. 4A-4C illustrate various operations performed by an example embodiment of a routine 400 to manage operations of an embodiment of the PRMTF system. The routine may be provided by, for example, execution of the PRMTF system 110 and/or PRMTF application 164 of FIG. 1, the PRMTF system 340 and/or PRMTF application 369 of FIG. 3, and/or a PRMTF system or application (not shown) performing the functionality illustrated with respect to FIGS. 2A-2D, such as to participate in the creation and display of various audiovisual artworks or other user activities via (for example) guided exercises (e.g., as part of one or more user interaction sessions), while managing, tracking and using human physiological responses to such exercises or other activity, as well as to perform other types of management operations in some situations.

In the illustrated embodiment, the routine begins at block 402, in which a request is received from a user of the PRMTF system (e.g., a user who has registered for or purchased access to the functionality of the PRMTF system, or is otherwise authorized to use the system, such as if any and all users are authorized in a particular embodiment and situation). The routine continues to block 404 to determine the type of request. If it is determined in block 406 that the type of request is other than to select an activity for performance by the PRMTF system, the routine proceeds to block 460 (in FIG. 4C) to determine the type of non-activity request that has been received from the user. If, however, the request is to select an activity, the routine continues to block 408 to determine the particular type of activity selected by the user.

In block 408, the routine determines whether the request is for a guided exercise within the PRMTF system (e.g., in a manner similar to that illustrated in the examples of FIGS. 2A, 2B and 2D). If not, the routine determines in block 410 that the request is to initiate or continue user-directed activities (e.g., the creation of audiovisual artwork) without such guidance, such as in a freeform or user-dictated manner (e.g., in a manner similar to that illustrated in FIG. 2C), and proceeds to block 412. Optionally, the PRMTF system may in block 412 initiate one or more guided physiological exercises before such user-directed activities occur by proceeding to block 430 (FIG. 4B), such as to effectuate physiological calming of the user prior to providing one or more activities for the user. Once the guided physiological exercise is completed, or if the user declines such guided exercise, in block 414 the routine initiates the presentation of tools and workspace in order to facilitate the user-directed activities by the user. During such activities or upon their completion, the routine proceeds to block 416 in order to optionally store the results (e.g., a created audiovisual artwork) for future use.

If it was determined in block 408 that the received request was for a guided exercise within the PRMTF system, in block 418 the routine determines whether the received request was to provide one or more guided exercises that include activities without physiological monitoring. If so, in block 420 the routine presents user options regarding available types of guided exercises offered by the PRMTF system, or automatically selects one or more such exercises, and proceeds to block 422 to initiate the user-selected or automatically selected exercises. In some embodiments, the available selections may include additional types of guided exercises available from an operator of the PRMTF system or other developers. The PRMTF system, for example, may enable users of the system to purchase or otherwise acquire various products and services from the PRMTF Web site and/or one or more partners of an entity operating the PRMTF system, such as to facilitate receiving additional content from or related to the users. As non-exclusive examples, the PRMTF system may make available additional guided drawing and/or physiological exercises; additional animated characters for use in such guided drawing and/or physiological exercises; additional artistic tools for use with the PRMTF system; additional background images, music, sound effects, animations, animation styles; physical prints or other physical media corresponding to audiovisual artworks; or other additional content. In various scenarios and embodiments, the PRMTF system may offer such additional content free of charge, or with charges incurred in various manners, such as per-item, in packaged collections, or subscription-based. As another example, the PRMTF system may provide the user with offers or opportunities to purchase one or more user tracking devices (such as those described elsewhere herein) to be integrated with the PRMTF system in collecting, integrating and analyzing user movements and/or user physiological indicators. In at least some embodiments, the advertising of such offers may be provided based on a variety of particular factors, such as information associated with the particular user, information associated with a client entity associated with the user, demographic information associated with a particular user and selected by the PRMTF system and/or the advertiser, etc.

In block 422, the routine proceeds to initiate the desired guided exercise activities. In certain embodiments, initiating the guided exercise may include doing so in accordance with one or more preferences specified or predefined by the user (e.g., target levels or values for one or more indicated types of physiological responses). Following the guided exercise, the routine proceeds to block 416 in order to optionally store any results of the guided exercise (e.g., audiovisual artwork created by the user as part of the guided exercise).

If in block 418 the routine determined that the received request was to initiate a guided exercise that includes activities with physiological monitoring by the PRMTF system, the routine proceeds to block 430 of FIG. 4B in order to identify one or more targeted physiological indicators or effects to monitor and optionally optimize or otherwise improve (e.g., based at least in part on information determined in block 422). For example, in certain scenarios the PRMTF system may present the user with options regarding whether the user would like the guided physiological exercise to promote calming, promote mental focus, heighten physical well-being, elevate mood, or some other desired effect. In other scenarios, the PRMTF system may present the user with options regarding whether they would prefer the guided physiological exercise to focus on a specific physiological indicator to control and/or monitor, such as breathing, heart rate, blood pressure, etc. As described elsewhere herein, in certain embodiments the PRMTF system may provide different options based on an age or other characteristic of the user, such as to present child users with only predefined or default options regarding the available exercises. In other embodiments and situations, the PRMTF system may select the one or more targeted physiological aspects, responses, target levels, indicators or effects without obtaining a selection or further input by the user, such as in an automated manner that is specific to the user (e.g., by using specified user instructions or preferences; by obtaining and/or analyzing information specific to the user, such as based at least in part on past interaction sessions with the user; etc.).

The routine then proceeds to block 432 in order to determine an appropriate activity for the targeted physiological indicator or effect, such as to determine an appropriate animation to use as part of a particular type of drawing activity, an appropriate amount of time for the activity, etc. Once the appropriate activity has been determined, the routine proceeds to block 434 to initiate the determined activity, including display of corresponding visual information (e.g., a determined animation, such as using an optimal animation rate in accordance with the targeted physiological indicator or effect), as discussed elsewhere herein with respect to the animated beach ball of FIG. 2D. In block 436, the routine optionally initiates a predefined audio program to accompany the animation in order to guide the user, although in other embodiments the user may select or otherwise influence such audio output. For example, the predefined audio program may comprise music, sound effects, vocal coaching (such as meditation coaching or other verbal guidance), etc. In other embodiments, other sensory outputs may be used (e.g., olfactory, haptic, taste, etc.), whether instead of or in addition to visual and/or audio output. The routine then proceeds to block 438, in which indications of one or more current physiological indicator measurements or values are received for the user. As one example, while targeting breathing rate for a particular guided physiological exercise, the PRMTF system may additionally monitor and track the user's heart rate, such as to gain additional data regarding the user's stress level aside from the rate at which the user is breathing.

Based on the indications received in block 438 of the user's current physiological indicators, in block 440 the routine modifies the display of the animation (and possibly the playback of any concurrent audio program or other sensory output) to reflect those current physiological indicators. In this manner, for example, the PRMTF system may provide audiovisual feedback for the user with respect to his or her attempt to optimize breath rate, heart rate, or other physiological indicator. In block 442, the routine compares the user's current physiological indicators with one or more desired values for those indicators. In block 444, the routine determines whether the current physiological indicators for the user are within a predetermined threshold of desired values for such indicators, such as to determine whether the user is progressing towards the desired value or values. In certain embodiments, the routine may additionally compare previous tracked values for the targeted or other physiological indicators, such as to provide the user with additional feedback regarding their progress over time. If it is determined that the user's current physiological indicators are not within the predetermined threshold, then the routine proceeds to block 445 to optionally modify the sensory outputs being used, and then proceeds back to block 438 in order to provide the user with more time for the guided physiological exercise and to receive additional indications of the monitored user's physiological indicators. In certain embodiments, the user or PRMTF system may also determine to pause or halt the guided physiological exercise, such as if a predetermined duration has elapsed, if the user becomes frustrated, etc.

Once the user's current physiological indicators fall within the predetermined threshold, or if the routine otherwise determines to proceed (e.g., based on an amount of time, based on completion of or other amount of progress in the activity, based on a user selection, etc.), the routine proceeds to block 446 to determine whether sufficient time has elapsed for the guided physiological exercise, such as to ensure that the user gains the benefit of the guided physiological exercise over some period of time. If not, then the routine proceeds back to block 438 to receive additional indications of the monitored user's physiological indicators. If it is determined in block 446 that sufficient time has elapsed for the guided physiological exercise, the routine proceeds to block 448 to optionally provide the user with feedback regarding the user's progress, such as based on previous results of earlier such exercises.

If it was determined in block 406 that the received request was not to select an activity for the user within the PRMTF system, the routine proceeds to block 460 in order to determine the type of non-activity request that has been received. In block 462, the routine determines whether the request is to receive information or to provide content; if so, the routine proceeds to block 464. If it is determined in block 464 that the request is not a request for digital content, the routine proceeds to block 466 and stores the provided user information for future use.

If it is determined in block 464 that the request is a request for digital content, the routine proceeds to block 468 and optionally provides information regarding multiple available options for such digital content. For example, if the request is received from a user via a client installation computing system), the routine may initiate the presentation of a digital catalog to enable the user to select from available audiovisual artworks that may be displayed. Alternatively, the routine may determine to provide information regarding available options for digital content if the received request does not specify such content as part of the request.

Based on the request and/or one or more user selections following the display of information in block 468, the routine proceeds to block 470 to determine whether the user is authorized to receive the particular digital content specified by the user. For example, the user may not be authorized to receive digital content other than that created by the individual user or a particular group of users, or the selected digital content may be available only for one or more fees. If it is determined in block 470 that the user is authorized to receive the specified digital content, the routine proceeds to block 472 to provide the specified digital content to the user, and then to block 474 in which the routine optionally displays the provide digital content for use with the PRMTF system. If it is determined in block 470 that the user is not authorized to receive such content, the routine proceeds to block 476 and prevents the transmission of the digital content.

If it was determined in block 462 that the request was not to receive information or provide content, the routine proceeds to block 478 to initiate the handling of another type of request. In block 480, the routine determines whether the particular request is supported for the authorized user from which it was received. If so, the routine proceeds to block 482 in order to perform appropriate functions to satisfy the request; if not, the routine proceeds instead to block 484 and denies the request. Non-exclusive examples of such requests include accessing stored profile information for a user, accessing previous monitored physiological response information for the user, ordering a print or other copy of a user-created artwork or other results of an activity by a user, etc.

After performing the described functionality with respect to blocks 448, 466, 474, 476, 482 or 484, the routine proceeds to block 495 (FIG. 4A) and determines whether to continue, such as until instructions to terminate are received, or until an end of a set of configured activities occur. If it is determined to continue, the routine returns to block 402 in order to await another request from an authorized user; if not, the routine proceeds to block 499 and ends.

In certain embodiments and scenarios, the PRMTF system may further provide various functionality for communications with or regarding its users. As non-limiting examples, the PRMTF system may provide user interface elements to allow users to set goals for progression within (or external to) the PRMTF system; may provide notifications to users for various reasons, such as to remind users of scheduled sessions with the PRMTF system; may integrate various communications for the user with respect to one or more social media services, including to share user-created audiovisual artworks or other digital content, send and receive textual or multimedia messages, or other relevant functionality.

Those skilled in the art will appreciate that the Web pages and other data structures discussed above may be structured in different manners, such as by having a single data structure split into multiple data structures or by having multiple data structures consolidated into a single data structure. Similarly, in some embodiments illustrated data structures may store more or less information than is described, such as when other illustrated data structures instead lack or include such information respectively, or when the amount or types of information that is stored is altered.

From the foregoing it will be appreciated that, although specific embodiments have been described herein for purposes of illustration, various modifications may be made without deviating from the spirit and scope of the invention. Accordingly, the invention is not limited except as by corresponding claims and the elements recited by those claims. In addition, while certain aspects of the invention may be presented in certain claim forms at certain times, the inventors contemplate the various aspects of the invention in any available claim form. For example, while only some aspects of the invention may be recited as being embodied in a computer-readable medium at particular times, other aspects may likewise be so embodied.

What is claimed is:

1. A computer-implemented method, comprising:
   determining a target multimedia artwork that was created by an original creation process, for use in connection with an interaction session with a user via at least one user device;
   causing the at least one user device to generate, as part of the interaction session, at least one audio output and at least one visual output to present an animated recreation of at least a portion of the target multimedia artwork in accordance with the original creation process;
   responsive to the animated recreation of the at least a portion of the target multimedia artwork as presented, obtaining one or more physiological responses of the user during the interaction session by using at least one hardware sensor of the at least one user device; and
   causing the at least one user device to modify, based at least in part on the one or more physiological responses, at least one of the audio output or visual output to further present an animated recreation of at least another portion of the target multimedia artwork.

2. The computer-implemented method of claim 1, further comprising obtaining data representing the original creation process of the target multimedia artwork.

3. The computer-implemented method of claim 2, wherein obtaining data representing the original creation process of the target multimedia artwork comprises recording, via at least one other user device, the original creation process of the target multimedia artwork.

4. The computer-implemented method of claim 1, wherein the target multimedia artwork was created by one or more other users.

5. The computer-implemented method of claim 2, further comprising using at least a portion of the data representing the original creation process of the target multimedia artwork as a basis for causing the at least one user device to generate the at least one audio output and at least one visual output to present an animated recreation of at least a portion of the target multimedia artwork.

6. The computer-implemented method of claim 2, wherein causing the at least one user device to generate the at least one audio output and at least one visual output to present an animated recreation of at least a portion of the target multimedia artwork comprises causing presentation of at least a portion of the animated recreation at a different speed than the original creation process of the target multimedia artwork.

7. The computer-implemented method of claim 1, wherein the target multimedia artwork includes at least one of a drawing or a song.

8. The computer-implemented method of claim 1, further comprising obtaining one or more user inputs, via the at least one user device, to create additional content for the target multimedia artwork.

9. The computer-implemented method of claim 8, further comprising causing at least one other user device to generate, as part of another interaction session, at least one audio output and at least one visual output to present an animated recreation of at least a portion of the target multimedia artwork that includes the additional content.

10. The computer-implemented method of claim 1, further comprising causing presentation of at least one of other audio or other visual information while at least a portion of the animated recreation of the target multimedia artwork is being presented.

11. One or more non-transitory computer-readable media collectively having stored contents that, when executed by one or more processors, cause the one or more processors to perform actions comprising:
  determining a target multimedia artwork that was created by an original creation process, for use in connection with an interaction session with a user via at least one user device;
  causing the at least one user device to generate, as part of the interaction session, at least one audio output and at least one visual output to present an animated recreation of at least a portion of the target multimedia artwork in accordance with the original creation process;
  responsive to the animated recreation of the at least a portion of the target multimedia artwork as presented, obtaining one or more physiological responses of the user during the interaction session; and
  causing the at least one user device to modify, based at least in part on the one or more physiological responses, at least one of the audio output or visual output to further present an animated recreation of at least another portion of the target multimedia artwork.

12. The one or more non-transitory computer-readable media of claim 11, wherein the actions further comprise obtaining data representing the original creation process of the target multimedia artwork.

13. The one or more non-transitory computer-readable media of claim 12, wherein obtaining data representing the original creation process of the target multimedia artwork comprises recording, via at least one other user device, the original creation process of the target multimedia artwork.

14. The one or more non-transitory computer-readable media of claim 11, wherein the actions further comprise obtaining one or more user inputs, via the at least one user device, to create additional multimedia artwork.

15. The one or more non-transitory computer-readable media of claim 14, wherein the actions further comprise causing at least one other user device to generate, as part of another interaction session, at least one audio output and at least one visual output to present the additional multimedia artwork.

16. A system, comprising:
  one or more processors; and
  one or more memories with stored instructions that, when executed by at least one of the one or more processors, cause the system to:
    determine a target multimedia artwork that was created by an original creation process, for use in connection with an interaction session with a user via at least one user device;
    cause the at least one user device to generate, as part of the interaction session, at least one audio output and at least one visual output to present an animated recreation of at least a portion of the target multimedia artwork in accordance with the original creation process;
    responsive to the animated recreation of the at least a portion of the target multimedia artwork, obtain one or more physiological responses of the user during the interaction session; and
    cause the at least one user device to modify, based at least in part on the one or more physiological responses, at least one of the audio output or visual output to further present an animated recreation of at least another portion of the target multimedia artwork.

17. The system of claim 16, wherein the instructions further cause the system to record, via at least one of the user device or another user device, the original creation process of the target multimedia artwork.

18. The system of claim 17, wherein the target multimedia artwork was created by one or more other users.

19. The system of claim 16, wherein the instructions further cause the system to record, as part of the interaction session, a creation process for additional multimedia artwork.

20. The system of claim 19, wherein the instructions further cause the system to cause presentation, via at least one of the user device or another user device, an animated recreation of at least a portion of the additional multimedia artwork.

* * * * *